(12) United States Patent
Laukkanen et al.

(10) Patent No.: US 9,955,928 B2
(45) Date of Patent: May 1, 2018

(54) CT APPARATUS FOR IMAGING CRANIAL ANATOMIES

(71) Applicant: PLANMED OY, Helsinki (FI)

(72) Inventors: Tapio Laukkanen, Espoo (FI); Sami Tohka, Helsinki (FI); Lauri Seppala, Helsinki (FI)

(73) Assignee: PLANMED OY, Helsinki (FI)

( * ) Notice: Subject to any disclaimer, the term of this patent is extended or adjusted under 35 U.S.C. 154(b) by 0 days. days.

(21) Appl. No.: 14/646,917

(22) PCT Filed: Nov. 22, 2013

(86) PCT No.: PCT/FI2013/051096
§ 371 (c)(1),
(2) Date: May 22, 2015

(87) PCT Pub. No.: WO2014/080083
PCT Pub. Date: May 30, 2014

(65) Prior Publication Data
US 2015/0289827 A1    Oct. 15, 2015

(30) Foreign Application Priority Data

Nov. 23, 2012 (FI) ...................................... 20120395

(51) Int. Cl.
*A61B 6/04* (2006.01)
*A61B 6/03* (2006.01)
(Continued)

(52) U.S. Cl.
CPC ............ *A61B 6/0421* (2013.01); *A61B 6/032* (2013.01); *A61B 6/035* (2013.01); *A61B 6/06* (2013.01); *A61B 6/501* (2013.01)

(58) Field of Classification Search
CPC ......... A61B 6/032; A61B 6/501; A61B 6/035; A61B 6/03; A61B 6/14; A61B 5/0555;
(Continued)

(56) References Cited

U.S. PATENT DOCUMENTS 4,850,003 A * 7/1989 Huebeck ................ A61B 6/501
378/177
5,642,392 A    6/1997 Nakano et al.
(Continued)

FOREIGN PATENT DOCUMENTS

DE    3627510 A    2/1988
EP    2123223 A1   11/2009
(Continued)

*Primary Examiner* — Brooke Purinton
(74) *Attorney, Agent, or Firm* — Fay Sharpe LLP (57) ABSTRACT

The invention relates to a medical computed tomography imaging apparatus which is especially designed to enable cranial imaging. The structure of the apparatus includes a gantry (2) comprising imaging means (21, 22) and a positioning support (8) which positioning support (8) is arranged to position the patient's cranium for exposure such that, when exposed, the cranium is scanned by a radiation beam substantially parallel with a plane formed by the facial area of the cranium and substantially only in an area on the facial side of the cranium.

20 Claims, 4 Drawing Sheets

(51) Int. Cl.
*A61B 6/00* (2006.01)
*A61B 6/06* (2006.01)

(58) Field of Classification Search
CPC ..... A61B 6/4452; A61B 6/4435; A61B 6/504; A61B 6/507; G06T 2207/10081; G06T 2207/30016; G06T 2207/30201
See application file for complete search history.

(56) References Cited

U.S. PATENT DOCUMENTS

| | | | |
|---|---|---|---|
| 6,052,428 | A | 4/2000 | Nakano et al. |
| 2006/0168732 | A1 | 8/2006 | Makino |
| 2009/0285356 | A1 | 11/2009 | Thoma et al. |
| 2010/0172468 | A1 | 7/2010 | Gregerson |
| 2012/0250821 | A1* | 10/2012 | Koehler ............... A61B 6/032 378/16 |
| 2013/0294673 | A1* | 11/2013 | Yamakawa ............ A61B 6/02 382/131 |
| 2015/0265365 | A1* | 9/2015 | Andrews ............ A61B 6/0421 600/411 |
| 2016/0128653 | A1* | 5/2016 | Fortuna ............... A61B 6/035 378/12 |

FOREIGN PATENT DOCUMENTS

| | | |
|---|---|---|
| GB | 2006590 A | 5/1979 |
| JP | 1995-275240 A | 10/1995 |
| JP | 2005-270329 A | 10/2005 |
| JP | 31-010898 U | 8/2006 |
| WO | 2011104439 A1 | 9/2011 |
| WO | 2011135187 A1 | 11/2011 |
| WO | 2011135192 A1 | 11/2011 |

* cited by examiner

CT APPARATUS FOR IMAGING CRANIAL ANATOMIES

FIELD OF INVENTION

The invention relates to a medical computed tomography imaging apparatus and a method for imaging a patient's cranial area in a novel way.

BACKGROUND OF INVENTION

Some specific imaging methods and, especially, imaging apparatuses designed for said methods have generally been used for x-ray imaging the human cranial area. Simplest of these as far as technology of the apparatus and of the imaging itself are concerned are solutions related to transillumination imaging in which, during an exposure, both the patient and the imaging means remain stationary. Thus, imaging of this kind has not always been implemented even such that the means for generating radiation and receiving image information would have been arranged as a physically integrated apparatus. On the other hand, e.g. in odontological panoramic imaging, controlling of the relative movement between the imaging means and the object being imaged plays an essential role, as well as does controlling of movement of a film or operation of a detector during exposure. A typical panoramic x-ray imaging apparatus is based on a structure in which a source of radiation and a receiver of image information are located at the opposite ends of the so-called C-arm, which is arranged movable. In one typical CT imaging, again, imaging means arranged inside a so-called gantry or an O-structure are moved within said structure while the patient is lying e.g. on a table belonging to the imaging apparatus, the table extends inside the gantry. Conventionally in these arrangements, either said table or the gantry itself is arranged movable to enable moving of the patient with respect to the imaging apparatus.

The medical use of computed tomography has broadened, inter alia, as a result of the so-called cone-beam tomography becoming more common such that, on the market, apparatuses have begun to emerge which have been specifically designed in view the needs of odontology and, on the other hand, orthopaedics, for example. Typically, these apparatuses are not as massive and as expensive as the conventional computed tomography apparatuses used in hospitals have been.

In apparatuses, in which a person has to be positioned inside a closed structure for the duration of an exposure, problems may occur due to claustrophobia suffered by some people. This problem is naturally potentially the greater the smaller the space within which the patient is to be positioned.

Even though computed tomography is in principle able to create voxel data of the whole volume being imaged, it has been noted that depending on the case some parts of an anatomy may become imaged more sharp than others. On the other hand, it is also known that some human tissues are more sensitive with respect to a radiation load than some others.

BRIEF DESCRIPTION OF INVENTION

The object of the present invention is to advance the state of the art by offering novel possibilities for cranial tomography. Especially, the object of the invention is an imaging apparatus arrangement which, depending on the embodiment of the invention and the prior art with which it is compared, can facilitate positioning of a patient in an examination opening of a ring-shaped imaging apparatus. This especially concerning patients who suffers from claustrophobia. The case may also be imaging of certain cranial anatomies in a novel way and, as a result, some anatomies may become imaged more sharp than in some imaging arrangements used before. On the other hand, some anatomies critical from the viewpoint of radiation load can be left partially or totally outside the radiation beam.

The essential characteristics of the invention are described in the accompanying patent claims. In embodiments of the invention, it is possible to arrange into connection with the examination opening of the imaging apparatus a positioning support designed in view of cranial imaging. The location of this positioning support in the examination opening can be arranged adjustable, also as motorized, and to be implemented in cooperation with controlling of moving of a ring-shaped O-arm. Thus, it is possible, inter alia, to facilitate moving of the imaging area (FOV—a field of view) with respect to the patient positioned ready for imaging. For clarity, it should be noted that, in this context, a positioning support means particularly a structure fastened to the imaging apparatus itself, not any external structure such as a movable table separate from the imaging apparatus by means of which a patient can be brought to the examination opening of the imaging apparatus. Furthermore, in preferable embodiments of the invention, it is possible to arrange to the examination opening of the apparatus an extension partially breaking its circular shape which, inter alia, provides more room for positioning a cranium for imaging.

With the method according to the invention, it is possible to acquire image information from the cranial area by an imaging scan which, due to the novel scan direction, might in some cases produce more sharp information from individual cranial anatomies and which offers new possibilities to decrease or avoid radiating tissues sensitive to radiation load.

Next, the invention and its preferable embodiments will be described in more detail and with reference to the attached figures.

DETAILED DESCRIPTION OF INVENTION

In the following, the terms centre and central axis will be used in connection with structures which do not necessarily form a true, full circle but are of circular shape only for their prevailing part. To avoid ambiguity, these terms refer in connection with this specification to a point and an axis which would be the centre or central axis of said structure in case the structure would form a full or a true circle.

Furthermore, concerning one component of the apparatus according to the invention, this specification employs the terms a substantially ring-shaped structure, an O-arm and a gantry. When the dimension in the direction of the central axis of this structure can be significantly large with respect to the diameter of said ring-shaped structure, for the avoidance of doubt it is stated that, in the following, the vertical position of the O-arm refers to a position where the central axis of the O-arm is horizontally oriented and the horizontal position of the O-arm refers to a position where its central axis is vertically oriented.

Figure 1:
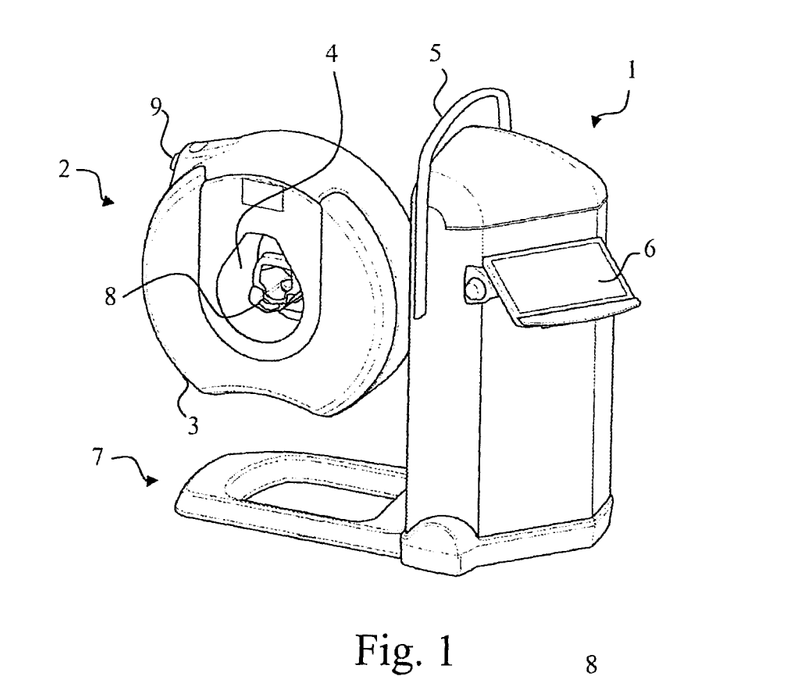
FIG. 1 shows a general view of an imaging apparatus a basic structure of which including a support structure, a substantially ring-shaped O-arm and a positioning support.

FIG. 1 shows a general view of an imaging apparatus according to the invention. The basic structure of the apparatus includes a support structure (1) which supports a substantially ring-shaped structure (2) within which imaging means (source of radiation 21, receiver of image information 22) of the apparatus are located. This O-arm (2) is arranged with an examination opening (4) within which an anatomy to be imaged is positioned. FIG. 1 further shows a patient support rail (5) arranged to the support structure (1), a user interface (6) being in functional connection with the control system of the apparatus, a possibly detachably mounted pedestal or base part (7) projecting substantially in the direction of the O-arm, and a positioning support (8) arranged to the examination opening (4).

The mounting of the structure (2) supporting the imaging means to the support structure (1) can be arranged to enable moving of the O-arm (2), such as adjustment of its height position. Preferably, the O-arm (2) is mounted to its support structure (1) from the side of the O-arm (2) and not below it, whereby no structures will be created below the O-arm (2) which could obstruct the use of the imaging apparatus and, possibly, positioning of a patient. The O-arm (2) can also be arranged to be turnable in at least one direction, preferably in both directions, in some embodiments up to 90 degrees from the vertical position shown in FIG. 1 to the horizontal position and, on the other hand, movable also in the horizontal direction. These movements may be realized with the help of one or more actuators (M0, M1) (FIG. 5) and control of these manoeuvres can be arranged implementable, aside from the user interface (6), also by means of a joy stick (9) arranged into connection with the O-arm (2) and/or the support frame (1).

Figure 2:
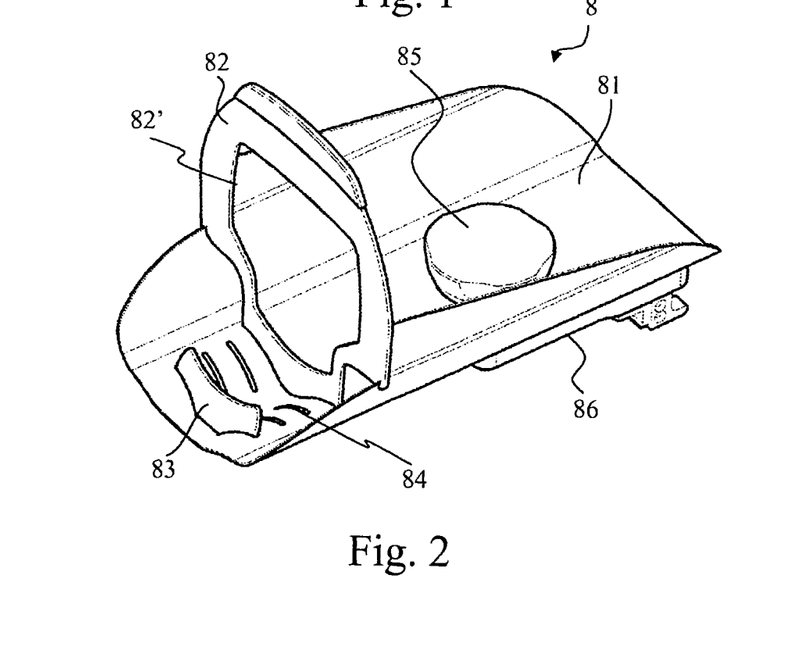
FIG. 2 shows one positioning support according to the invention.

The positioning support (8) shown in FIG. 2 comprises a trough-shaped support structure (81) and a forehead support (82) diverging substantially perpendicularly from it. The forehead support (82) is arranged with an opening, a viewing opening (82') which is preferably positioned at least substantially on the height of the patient's eyes. Because the patients' anatomies can be of different sizes and different shapes, the front part of the trough-shaped support structure (81), i.e. the area where the patient's jaw will be positioned, is arranged with incisions (84) which enable a detachable mounting of an adjusting plate (83) to the support construction (81). There can be incisions (84) in different sections of the front part of the support structure (81) and, on the other hand, there can be different adjusting plates (83). These adjusting plates (83) which are to be placed in incisions arranged to the through as such are still only one preferable embodiment of the invention, as one can also arrange the positioning support (8) with other kind of means (83, 84) for adjusting location of one or more support points provided by the positioning support (8).

In the embodiment according to FIG. 2, into connection with the positioning support (8) is also arranged an adjusting knob (85) to enable adjusting of position of the positioning support with respect to the examination opening (4). The adjusting knob (85) can be arranged to operate as a screw which tightens one or more guide grooves (not shown in the figure) arranged at a desired point in a connection structure (86). Opening of this screw then enables moving the positioning support (8) to a new desired point in said guide groove. The adjusting knob (85) can also be arranged to operate as a joy stick by means of which location of the positioning support (8) in the examination opening (4) can be adjusted.

The adjustment of the position of the positioning support (8) in the examination opening (4) can mean, inter alia, moving it in the direction of the central axis of the examination opening, in a direction perpendicular with respect to it or tilting the positioning support (8). Such manoeuvring possibilities provide flexibility in positioning an anatomy for imaging. By arranging the patient support (8) detachably mounted, the apparatus can be mounted with different positioning supports (8), which enables always using a positioning support (8) according to the special characteristics of the imaging in question and, besides cranial anatomies, imaging of extremities, for example.

Naturally, the positioning support (8) can be realized as a structure different of its details than as those shown in FIG. 2. What is essential is that it provides such support points to position a cranium for imaging that the cranium is positioned in the imaging apparatus in a desired way.

Figure 3:
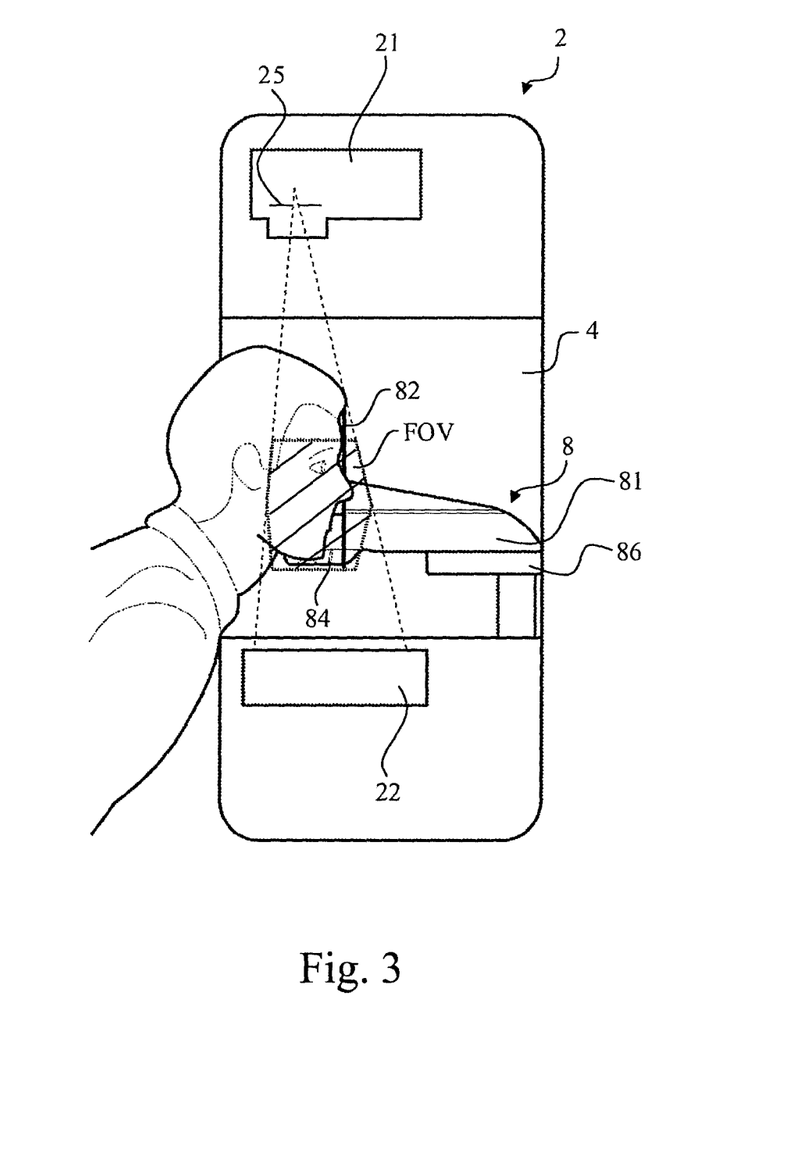
FIG. 3 shows positioning of an anatomy being imaged in one imaging apparatus according to the invention.

FIG. 3 shows a patient positioned in one imaging apparatus arrangement according to the invention. The positioning support (8) shown in FIG. 3 is in principle equivalent to the one in FIG. 2 but, to keep FIG. 3 as simple as possible, the positioning support (8) is shown partially simplified. The figure shows how the patient's forehead supports itself on the forehead support (82) of the positioning support (8) and the jaw to the bottom of the through-shaped support construction (81). In the example of FIG. 3, the patient's cranium is large, whereby the adjusting plate (83) is not in use.

FIG. 3 shows that the patient's gaze is directed forward (via the opening in the forehead support (82) shown in FIG. 2), not upward towards the inner surface of the examination opening (4), which would locate substantially close to the patient's eyes which some people could find anguishing. On the other hand, FIG. 3 shows positioning of a plane formed by the patient's face with respect to a radiation beam—or to a plane not shown in the figure as such which will be formed when the imaging means (21, 22) are moved within said substantially ring-shaped structure (2) which supports the imaging means.

FIG. 3 also shows a collimator (25) arranged into connection with the source of radiation (21), which comprises a two-dimensional opening which limits the radiation being emitted from the focus of the source of radiation into a two-dimensional and expanding radiation beam. The volume (FOV—Field of View) shown in FIG. 3 illustrates the part of the cranial anatomy one is able to image by a radiation beam limited by the collimator (25) in the construction according to FIG. 3, when the imaging means (21, 22) move during an exposure within the gantry (2) with respect to a rotation axis defined by the central axis of the gantry.

Generally, the volume being imaged with the arrangement according to the invention can thus be made to include the jaw and the jaw joints, teeth and ears as well as maxillary and frontal sinuses, i.e. anatomies substantially on the facial side of a cranium. On the other hand, the thyroid gland, which is critical for radiation load caused to a patient, can still be positioned to remain outside the volume being imaged.

The embodiment of the invention shown in the attached figures comprises some arrangements different from the usual as far as the gantry of the apparatus is concerned, too. When looking at a cross-section perpendicular to the direction of the central axis of the O-arm (2) shown in FIG. 1, i.e. the radial cross-section of the O-arm (2), an outer cover (3) of the O-arm (2) forms for its prevailing part a shape of a circle which yet comprises a sector where the distance from the centre of said circle to the edges of the outer cover (3) is smaller than the radius of the prevailing part of the shape of a circle. In the embodiment of the invention according to FIG. 1, the part in said sector with the cut out of the O-ring (2) is evenly curved in the opposite direction with respect to the arch of the circle of the prevailing portion of the outer cover (3), but this cut out can also be of some other shape, such as wedge-shaped, rectangular, straight or even curved in the same direction as the portion of the arch of the outer cover (3) substantially of the shape of a circle.

When the sector of the kind described above is arranged in a section of the O-arm (2) substantially orientating downwards or being orientable downwards, implementing e.g. a cranial imaging may be easier in the sitting position as it would be without such solution.

In the embodiment of the invention according to FIG. 1, the examination opening (4) is also implemented only for its prevailing part substantially as a circle. A sector is arranged to the examination opening (4) which forms an extension to the circle. That is, the examination opening (4) is provided with a sector in the area of which the distance of the edge of the examination opening (4) from the centre of the circular portion of the examination opening (4) (or from the central axis of the O-arm (2)) is longer than the radius of the circular portion of the examination opening (4). Such design of the examination opening (4) is preferable e.g. when the aim is to realize dimensions of the cross-section perpendicular with respect to the central axis of the O-arm (2) as small as possible. It also gives more space for positioning e.g. an anatomy of oval shape (i.e. a cranium but as well a foot) to the examination opening (4). In such an embodiment of the invention, we can talk about e.g. an examination opening (4) the diameter of the portion of the shape of an arch of a circle of which is e.g. of the order of 30-35 cm. In the preferable embodiment of the invention according to FIG. 1, the examination opening (4) is substantially of the shape of a droplet, i.e. the shape of its extension is substantially an equilateral triangle having a truncated apex, but said extension can naturally be of some other shape as well.

The above-described shapes of the outer cover (3) of the O-arm (2) and the examination opening (4) different from the circular shape are part of a preferable embodiment of the invention, but the outer cover (3) can also be implemented in some other shape.

Figure 4:
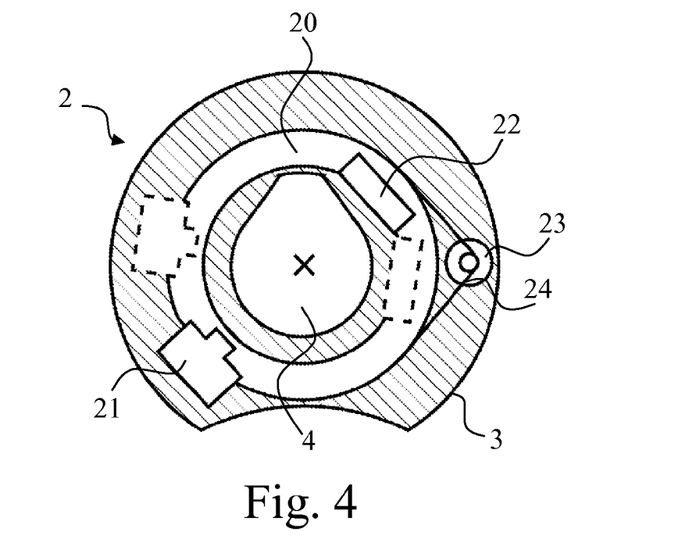
FIG. 4 shows one arrangement applicable for use in connection with the invention for arranging imaging means to a ring-shaped imaging part.

In the apparatus shown in the attached figures, the source of radiation (21) and the receiver of image information (22) are arranged within the substantially ring-shaped structure (2) supporting the imaging means and as movable along a curved path within said structure, substantially on opposite sides of the examination opening (4). The distance between the edge of the examination opening (4) and the outer cover (3) of the O-arm (2) (or the radial dimension of the ring of the O-arm) must naturally be arranged of adequate size to enable said paths. FIG. 4 shows a possible embodiment of the invention which includes a ring-shaped support part (20) arranged within the O-arm (2), whereto substantially on sides opposite to each other are arranged the source of radiation (21) and the receiver of image information (22). The support part (20) is arranged rotatable within the structure (2) supporting the imaging means by means of an actuator (23) and a transmission belt (24). Thus, it is possible to image the anatomy positioned at the examination opening (4) from different directions within the range of an angle of rotation of the imaging means and, from the image information thus acquired, to create a voxel model of the object by means of image-data processing methods known as such.

In a preferable embodiment of the invention according to FIG. 4, the source of radiation (21) and the receiver of image information (22) are arranged movable within said substantially ring-shaped structure (2) supporting the imaging means with respect to the centre of rotation such that the source of radiation (21) (the focus of the source of radiation) moves at a different distance from said centre of rotation than the receiver of image information (22). In the arrangement according to FIG. 2, the source of radiation (21) is mounted to the outer circumference of the ring-shaped support part (20) whereby, when rotating the support part (20), the focus of the source of radiation (21) moves as farther from said centre of rotation than the receiver of image information (22) mounted to the side of the inner circumference of the support part (20). When the receiver of image information (22) is thus brought closer to the volume being imaged, it is possible when using a detector (22) of given size to use a wider radiation beam and thus increase the volume being imageable as compared with that the receiver of image information (22) were to move as farther from the object.

According to one preferable embodiment of the invention, the range of movement of the imaging means is implemented unlike in some prior-art apparatuses of similar type, i.e. by arranging the source of radiation (21) and the receiver of image information (22) movable along a curved path substantially on opposite sides of the examination opening (4) for a shorter distance than 360 degrees. This distance is referred to in the context of this specification as an angle of rotation, and preferably it is arranged to be somewhat larger than 180 degrees but still substantially smaller than 360 degrees, such as of the order of 210±20 degrees. Then, arranging the imaging means (21, 22) to be movable at different distances from the centre of rotation may preferably be implemented particularly in an arrangement comprising the above-described cut in the O-arm (2) and extension in the examination opening (4). The range of manoeuvring of the source of radiation (21) can be arranged not to extend to that sector of the O-arm in which the outer cover (3) is cut like described above and, on the other hand, the range of manoeuvring of the receiver of image information (22) not to extend to that sector of the O-arm (2) in which is arranged the extension of the examination opening (4) as described above. When the utmost dimensions of said extension and cut from the centre of rotation of the imaging means are arranged appropriate with respect to those different distances at which the imaging means are rotated from the centre of rotation, the apparatus can be implemented as shown in FIG. 3 such that the source of radiation (21) arranged to move as farther from the centre of rotation is able to move from the outside of the extension of the examination opening (4) and the receiver of image information (22), again, from the inside of the cut arranged to the outer cover (3) of the O-arm (2).

Especially, such embodiment of the invention enables a structure where, due to the extension arranged to the examination opening (4), it is possible to implement the diameter of the circular portion of the examination opening (4) smaller than would be possible without the extension sector and, further, it is possible to arrange the cut to the outer cover (3) of the O-arm (2) which facilitates patient positioning. Such an embodiment of the invention is implementable as a compact structure and it enables realizing both the examination opening (4) and the outer dimensions of the whole O-arm (2) smaller than would otherwise be possible.

Figure 5:
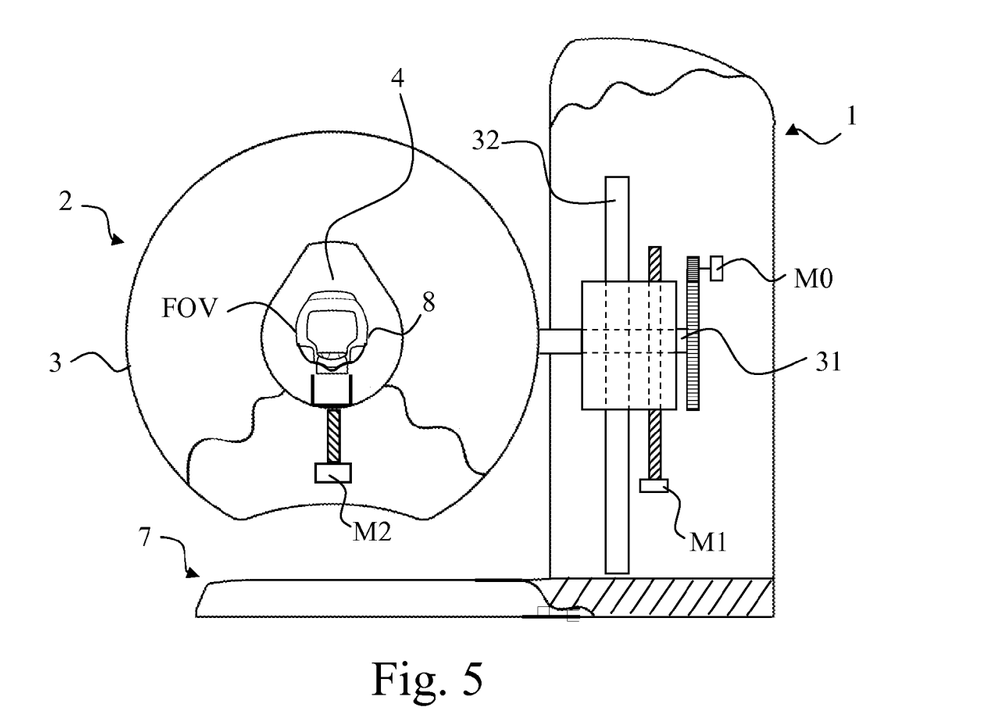
FIGS. 5 and 6 show arrangements for motorized moving of some components of the apparatus.

Above, we already referred to moving of the components of the apparatus and to FIG. 5. According to a preferred embodiment of the invention, the adjustment of the height position of the positioning support (8) the adjustment of location of the positioning support (8) with respect to the central axis of the O-arm (2)) can be arranged motorized and, besides, to function as synchronized with the adjustment of height position of the O-arm (2). Thus, the positioning support (8) can be driven to its lowermost (or some other desired) position with respect to the O-arm (2) with the help of the actuator (M2), and the O-arm (2) with the help of the actuator (M1) to such a height position in which the positioning support (8) being at its lowermost position will get positioned at the height level whereon one wishes it to be during imaging. The positioning support (8) driven to its lowermost position leaves more room within the examination opening (4) for positioning an anatomy and, after one has managed to get it positioned in a desired manner, the arrangement can be brought ready for imaging by driving the positioning support (8) upwards and the O-arm (2) downwards at an equal speed. This way, the positioning support (8) and thus also the patient remain stationary with respect to "the patient's set of coordinates" while, at the same time, the area to be imaged—or rather, the volume (FOV)—moves to a desired place with respect to the anatomy having been positioned at the positioning support (8).

FIG. 5 also shows a joy stick (32) belonging to the structure for driving the O-arm (2) to different height positions and a horizontal axis (31) with respect to which the O-arm (2) is arranged turnable, preferably turnable in both directions from its vertical position shown in FIG. 5. The structure for driving the O-arm (2) in the horizontal direction can be implemented in a corresponding way but, to keep FIG. 5 simplified, this structure is not shown in the figure. Versatile degrees of freedom of motion of the gantry (2) can facilitate patient positioning, inter alia, in connection with imaging of patients of anatomies different from the average, or of injured patients.

Figure 6:
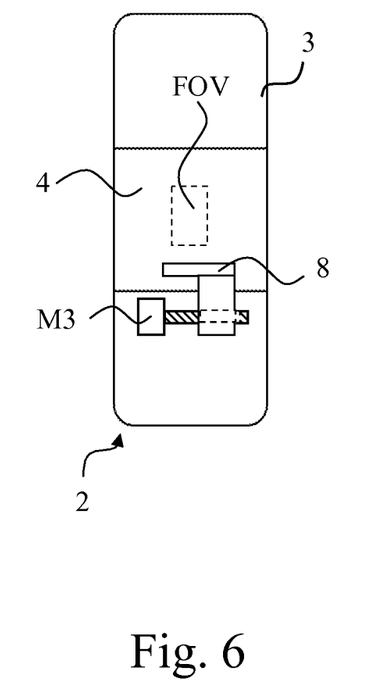

FIG. 6 shows, as simplified, yet another embodiment for adjusting location of the positioning support (8) with respect to the O-arm (2). In this arrangement, a motorized (M3) freedom of movement parallel with the direction of the central axis of the O-arm (2) is arranged for the positioning support (8). This arrangement enables, inter alia, to move location of the imaging area (FOV) with respect to the patient by synchronized drive of the positioning support (8) and the O-arm (2) in opposite directions, whereby the positioning support (8) remains stationary with respect to the patient's set of coordinates.

According to a preferable embodiment of the invention, the apparatus includes a control system which can comprise a control function for moving the positioning support (8) by at least one actuator in the first direction and at the first speed within the area of the examination opening of the substantially ring-shaped structure (2) which supports the imaging means, and for simultaneously moving the ring-shaped structure (2) supporting the imaging means with respect to said support construction (1) by at least one actuator substantially at said first speed substantially in the opposite direction than said first direction. According to a preferable embodiment of the invention, the movement of the positioning support (8) in the first direction can comprise moving of the positioning support (8) substantially in a direction perpendicular to the direction of the central axis of said ring-shaped structure (2) towards the central axis of the examination opening (2). Thus according to different preferable embodiments, when the structure (2) supporting the imaging means is at the vertical orientation, said movement of the positioning support (8) in the first direction can comprise moving the positioning support (8) in the vertical direction, whereupon said movement of the structure (2) supporting the imaging means in the opposite direction comprises vertical movement of the structure (2) supporting the imaging means with respect to its said support construction (1).

Considering imaging to be performed by the apparatus, the angle of rotation of the imaging means (21, 22) previously described above is sufficient in cone-beam tomography in which the radiation beam generated by the source of radiation (21) is arranged to be limited to a true two-dimensional radiation beam and the receiver of image information (22), again, of its form and dimensions at least such that it covers said two-dimensional radiation beam. In an apparatus according to the invention, a radiation beam of this kind can also be arranged to be limited to more than one size and/or shape, whereby the receiver of image information (22) must naturally be arranged either to cover all possible radiation beam sizes and shapes or it must be arranged changeable.

The base part (7) arranged mountable into connection with the support construction (1) shown in FIG. 1 can be a component optionally arranged to the apparatus and its use is preferable particularly when there is no intention to bolt or otherwise mount the support construction (1) on the floor, or if the location where the apparatus is considered to be used does not enable floor mounting. The base part (7) assists the apparatus staying upright and, at the same time, it is e.g. possible to arrange wheels under the projecting base part (7) and the support construction (1) to facilitate transferring of the apparatus, such as transferring it from one imaging room to another. Considering these various possible ways to install the apparatus, it is preferable to arrange the base part (7) detachably mountable to the support construction (1) of the apparatus.

The preferable embodiment of the invention shown in FIG. 1 can be implemented as a relatively compact structure and, for achieving many of the advantages described above, as a structure where the radius of the prevailing portion of the examination opening (4) being of the shape of an arch of a circle is of the order of 15 cm or slightly more and, on the other hand, the radius of the prevailing portion of the O-arm (2) of the shape of an arch of a circle is of the order of 50 cm or even less. Here, the distance of the focus of the source of radiation (21) from the centre of rotation of the imaging means (21, 22) can preferably be arranged e.g. for about 390 mm and that of the receiver of image information for about 190 mm.

Even though the present invention can be considered to be applicable also in connection with conventional, large apparatuses designed for imaging the whole human body, the unexpectedness and benefits of the arrangement are emphasized in a context in which the relative positioning of the imaging means (source of radiation and receiver of image information) and the dimensions of the receiver of image information are implemented to produce an imaging area (FOV) the volume of which is smaller than the volume of the human cranium (i.e. e.g. smaller than 4 $dm^3$).

Above, we discussed in connection with the description related to FIG. 3 the essential feature of the invention, i.e. how the positioning support (8) is arranged to position the anatomy being imaged to the apparatus. In more detail, it can be said that it is essential that the support points according to the invention provided by the positioning support (8) are dimensioned in accordance with the dimensions of the human cranium and the positioning support (8) is arranged into connection with the examination opening (4) such that, a human being positioned in the positioning support (8), the human face is pointing towards an angle area "central axis of the examination opening (4) of ±45 degrees", and/or such that the plane formed by the human face is parallel with or in the angle area of ±45 degrees with respect to the plane which is formed by the imaging means (21, 22) when moving within the substantially ring-shaped structure (2). Preferably, this is implemented particularly such that relative positioning of the imaging means (21, 22) and dimensions of the receiver of image information (22) and, on the other hand, said positioning support (8) are realized such that the volume getting imaged (FOV) by an exposure will be located, with respect to the anatomy being positioned at the positioning support (8), within an area substantially on the facial side of the cranium.

The support points provided by the positioning support (8) can be arranged to be located, in the direction of the central axis of the examination opening (4), at a distance from the edge of the examination opening (4) within the examination opening (4). Preferably, at least one support point is arranged to be formed substantially in the jaw area and at least one substantially in the forehead area. The positioning support (8) can be arranged with means for adjusting location of one or more of said support points (83, 84), and location of the positioning support (8) in the examination opening (4) adjustable in the direction of the central axis of the examination opening and/or in the perpendicular direction with respect to it. The positioning support (8) can also be arranged tiltable.

The general purpose of the positioning support according to the invention is to provide for the human cranium support points in order for the patient's head better remaining stationary during an exposure. One of the design criteria and object of the invention was to offer a possibility to remove possible anxieties a patient may have by emphasizing the fact that, if needed, it is easy, quick and effortless to exit the patient support according to the invention by just pulling one's head backwards. At the same time, the novel patient positioning creates possibilities for novel imaging geometries with respect to the patient's anatomy by imaging apparatuses of the kinds known in the prior art as such.

In the light of the description above, the invention thus also relates to a method for collecting image information from the cranial area, in which method, the cranium is positioned for imaging and an exposure is implemented by a two-dimensional radiation beam which is driven around the cranium for at least 180 degrees and the radiation having penetrated the cranium is detected by a detector moving on the opposite side of the cranium, in which method, the anatomy is scanned by a radiation beam substantially parallel with the plane formed by the facial area of the cranium and substantially only in the area of the facial side of the cranium.

It is obvious for one skilled in the art that as for its details, the present invention may be implemented also in other ways than according to the embodiments of the invention described above.

The invention claimed is:

1. A method for collecting image information from a cranial area of a human patient, comprising:
   providing a ring shaped structure supporting a source of radiation,
   positioning at least a part of a cranium of the patient for imaging in the ring shaped structure such that the patient's face enters an opening in the ring shaped structure from one side and extends toward an opposed side of the opening during an exposure of radiation,
   implementing the exposure of radiation using a two-dimensional radiation beam which is driven around the ring shaped structure for at least 180 degrees and scans a face side of the cranium such that a volume being imaged by the exposure of radiation is located only within an area on the face side of the cranium, and
   detecting the radiation having penetrated the face side of the cranium by a detector moving on the opposite side of the ring shaped structure.

2. The method according to claim 1, characterized in that a positioning support is arranged to be located in the direction of a central axis of an examination opening of an imaging apparatus used for collecting the image information at a distance from an edge of the examination opening.

3. The method according to claim 2, characterized in that said positioning support is arranged to form at least one support point in a jaw area and at least one in a forehead area.

4. The method according to claim 2, characterized in that said positioning support comprises a forehead support extending perpendicularly with respect to the central axis of the examination opening.

5. The method according to claim 4, characterized in that said forehead support is arranged with a viewing opening.

6. The method according to claim 2, characterized in that said positioning support is adjustable.

7. The method according to claim 2, characterized in that location of said positioning support in the examination opening is adjustable in the direction of the central axis of the examination opening and/or in a perpendicular direction.

8. The method according to claim 2, characterized in that said positioning support is arranged movable in a perpendicular direction with respect to the central axis and/or in a direction which is parallel with the direction of said central axis.

9. The method according to claim 2, characterized in that said positioning support is arranged movable by means of at least one actuator secured to a structure of an imaging apparatus used for collecting the image information supporting the detector.

10. The method according to claim 9, wherein said imaging apparatus used for collecting the image information includes a control system which comprises a control function for moving the positioning support by at least one actuator in a first direction and at a first speed within the area of an examination opening and for simultaneously moving the structure supporting the detector by at least one actuator at said first speed in the opposite direction than said first direction.

11. The method according to claim 10, characterized in that said movement of the positioning support in the first direction comprises moving of the positioning support in a direction perpendicular to the direction of the central axis towards the central axis of the examination opening.

12. The method according to claim 2, characterized in that a structure forming the examination opening is arranged turnable with respect to a horizontal axis in one or both directions from its vertical position and/or adjustable as of its height position.

13. The method according to claim 2, characterized in that mutual positioning of the radiation beam and detector of an imaging apparatus used for collecting the image information are implemented to produce an imaging area field of view the volume of which is smaller than 4 dm$^3$.

14. The method according to claim 1 characterized by that in the method an imaging apparatus is used which includes a support structure, which is arranged to support a substantially ring-shaped structure supporting imaging means, which imaging means include a source of radiation and a receiver of image information, which imaging means are arranged within said substantially ring-shaped structure supporting the imaging means on opposite sides of each other and movable within said ring-shaped structure supporting the imaging means, a collimator arranged into connection with the source of radiation to limit the radiation emitting from a focus of the source of radiation into a two-dimensional and expanding radiation beam, in which apparatus said ring-shaped structure supporting the imaging means includes an examination opening into which an object to be imaged is positionable for imaging and within which is arranged a positioning support for supporting an anatomy being imaged for duration of an exposure.

15. The method according to claim 14, characterized by the method comprising a patient positioning stage performed prior to the exposure in which a patient is positioned in the positioning support arranged in said examination opening, in connection with which patient positioning at least one of the following is implemented: moving the positioning support in the examination opening, turning the ring-shaped structure supporting the imaging means with respect to a horizontal axis, moving the ring-shaped structure supporting the imaging means upwards and/or downwards, moving the ring-shaped structure supporting the imaging means in a horizontal direction.

16. The method according to claim 1, wherein the area substantially on the face side of the cranium consists of an area of the cranium extending from an imaginary line between the patient's ears to the patient's nose.

17. The method according to claim 1, wherein the volume being imaged excludes a thyroid gland.

18. A method for collecting image information from a cranial area of a human patient, comprising:
providing a ring shaped structure supporting a source of radiation;
positioning a cranium of the patient for imaging in the ring shaped structure, such that the patient face enters a hole in the ring from one side and faces out the other side of the hole during radiation;
implementing exposure by a two-dimensional radiation beam which is driven around the cranium for at least 180 degrees, radiates parallel to a plane formed by 3 points on the circumference of the ring shaped structure and scans only from a face side of the cranium; and
detecting the radiation having penetrated the cranium by a detector moving on the opposite side of the cranium.

19. A method for collecting image information from a cranium of a human patient, the method comprising providing a ring shaped structure residing in a vertical plane, said ring shaped structure further defining a cranium receiving passage wherein the patient's face enters one side of the passage and extends toward an opposed side of the passage, said passage having a longitudinal axis;
positioning the cranium for imaging against a forehead support disposed within the cranium receiving passage such that said cranium penetrates only partially into said passage, said forehead support defining a cranium receiving surface perpendicular to said longitudinal axis;
providing a radiation beam source within said ring shaped structure and a detector moving on the opposite side of the ring shaped structure; and,
imaging only a region of the cranium abutting the forehead support by at least 180 degrees rotation of the radiation beam.

20. The method according to claim 19, wherein the region being imaged excludes a thyroid gland.

* * * * *